US00PP21511P3

(12) United States Plant Patent

Tupy et al.

(10) Patent No.: US PP21,511 P3

(45) Date of Patent: Nov. 23, 2010

(54) COLUMNAR APPLE TREE NAMED 'MOONLIGHT'

(50) Latin Name: *Malus domestica* (Borkh.)
Varietal Denomination: Moonlight

(75) Inventors: Jaroslav Tupy, Prague 6 (CZ); Otto Louda, Pencin u Liberce (CZ); Jan Zima, Turnov (CZ)

(73) Assignee: Institute of Experimental Botany, AS CR, v.v.i. (UEB), Prague (CZ)

( * ) Notice: Subject to any disclaimer, the term of this patent is extended or adjusted under 35 U.S.C. 154(b) by 0 days.

(21) Appl. No.: 12/319,457

(22) Filed: Jan. 7, 2009

(65) Prior Publication Data

US 2010/0175158 P1 Jul. 8, 2010

(51) Int. Cl.
*A01H 5/00* (2006.01)

(52) U.S. Cl. ..... Plt./175

(58) Field of Classification Search ..... Plt./172, Plt./161, 175
See application file for complete search history.

(56) References Cited

OTHER PUBLICATIONS

Upov-rom Plant Variety Database. GTI Jouve Retrieval System 2009/05. Citation for Malus 'Moonlight' 3 pp.*

* cited by examiner

*Primary Examiner*—June Hwu
(74) *Attorney, Agent, or Firm*—The Webb Law Firm

(57) ABSTRACT

A new and distinct *Malus domestica* (Borkh.) apple tree variety is provided which exhibits a columnar tree type, weakly vigorous compact growth, predominant bearing on spurs and $V_f$-resistance against scab. The new variety yields late maturing, medium-sized, globose-conical to conical fruits having good storage quality. The fruit color is yellow-green to yellow with a partial red to orange blush. The fruits have a yellow-colored firm flesh that is crisp and juicy with a good sweet/sour balance and very good eating quality.

6 Drawing Sheets

Botanical classification: *Malus domestica* (Borkh.).
Varietal denomination: 'MOONLIGHT'.

BACKGROUND OF THE INVENTION

The present invention comprises a new and distinct cultivar of apple tree botanically classified as *Malus domestica* (Borkh.) and known by the varietal name 'MOONLIGHT'. The new variety is the result of a cross between 'Goldstar' (female parent, unpatented) and 'Telamon' (aka, Waltz) (male parent, U.S. Plant Pat. No. PP6,224). The cross resulting in 'MOONLIGHT' occurred in the Spring of 1996 at 310 meters above sea level with a mean annual temperature of 7.7° C. and a mean annual precipitation of 680 mm. The purpose of the breeding program was to develop late, dessert, disease resistant varieties with a columnar tree type. The new variety was discovered in the Fall of 2002 with the first fruiting of the original seedling in The Czech Republic. Subsequently, the new variety was asexually reproduced at the Institute of Experimental Botany AS CR, v.v.i., Station Strizovice, 45 Pencin u Liberce in The Czech Republic by budding/grafting on apple rootstocks in the Spring of 2003.

The new variety is similar to 'Goldstar' in yellow-green to yellow fruit color and in that it exhibits the presence of $V_f$-resistance against scab. However, 'MOONLIGHT' differs from its female parent, as 'Goldstar' is a ramified tree type and the present variety is a columnar tree type. Further, the new variety has a globose-conical to conical fruit shape, while 'Goldstar' has an obloid fruit shape. The new variety is similar to 'Telamon' in tree type and its compact, dense growth habit with short internodes. However, the new variety is different from 'Telamon' as its fruit overcolor is absent or has a slight red to orange blush, while 'Telamon' has fruit with 50% red to purple solid flush. Further, the new variety has a longer fruit stem (30 mm vs. 16 mm) and deeper stalk cavity (14 mm vs. 9 mm) than 'Telamon'. Additionally, the new variety is similar to apple tree variety 'Golden Delicious' (unpatented) in fruit shape, fruit stem length, and yellow-green to yellow ground color of fruits. However, the new variety differs from 'Golden Delicious' in tree type as 'Golden Delicious' has a ramified tree type. Further, the internode length of 'MOONLIGHT' is shorter than that of 'Golden Delicious'. Finally, the presence of $V_f$-resistance against scab also distinguishes the new variety from 'Golden Delicious'. The following characteristics also distinguish the new variety from other varieties known to the breeders:

- Late, dessert-type, diploid variety;
- Columnar tree type;
- Trees exhibit weak vigor;
- The growth habit is compact and dense with very short internodes;
- Medium-sized fruits;
- Globose-conical to conical fruit shape;
- The fruit ground color is yellow-green to yellow;
- Slight red to orange blush of overcolor with some fruits;
- The fruit flesh is yellow, firm, crisp, and juicy with a well-balanced sugar to acid ratio; and
- $V_f$-resistance against scab.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type. It should be noted that colors may vary with growing conditions and time of year.

DESCRIPTION OF THE PLANT

Figure 1:
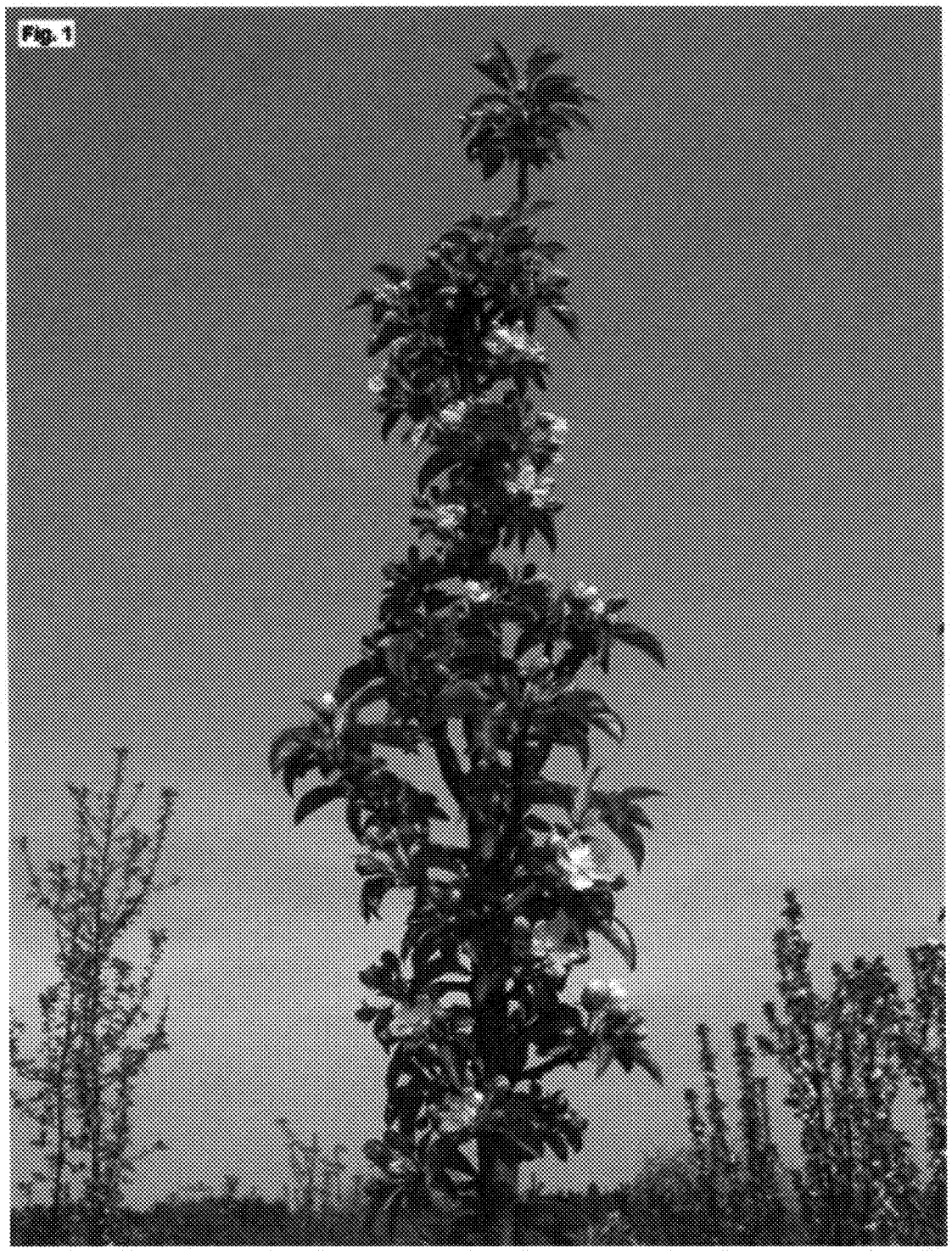
FIG. 1 is a photograph of the original tree of the new variety, showing canopy form at blossoming time.
Figure 2:
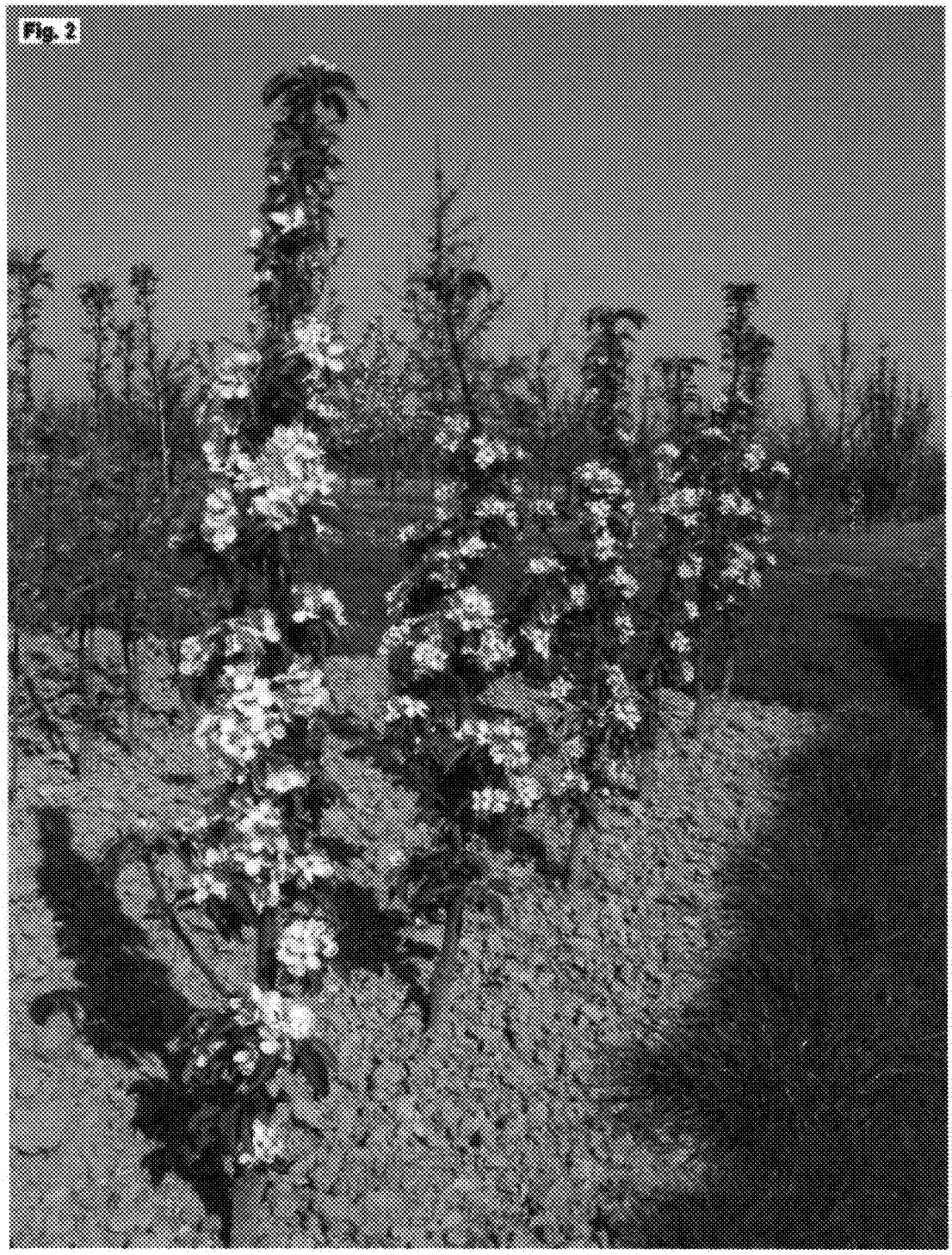
FIG. 2 shows young, flowering trees of the new variety on MM 106 rootstock.
Figure 3:
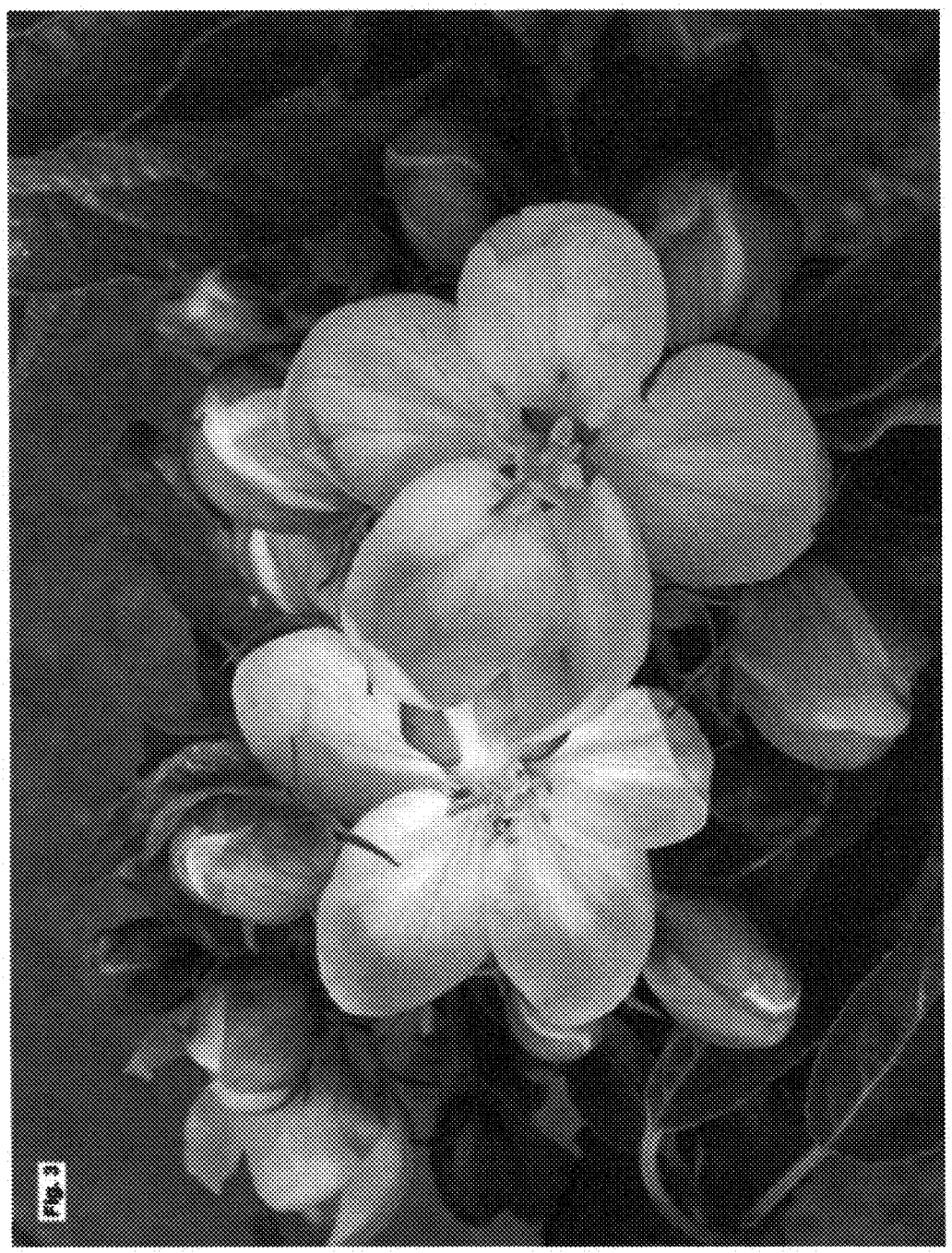
FIG. 3 shows the blossoms of the new variety.
Figure 4:
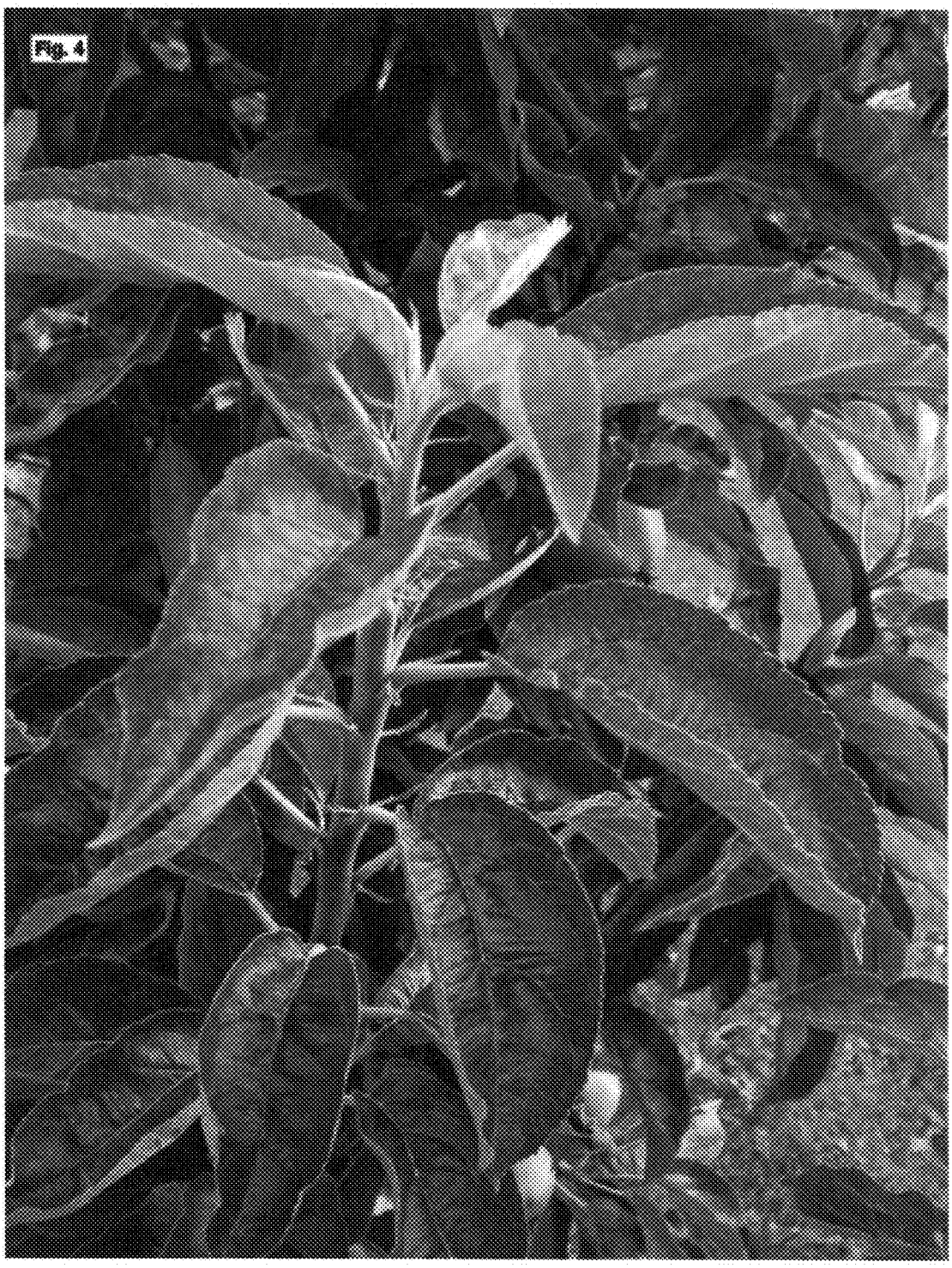
FIG. 4 shows a growing shoot of the new variety.
Figure 5:
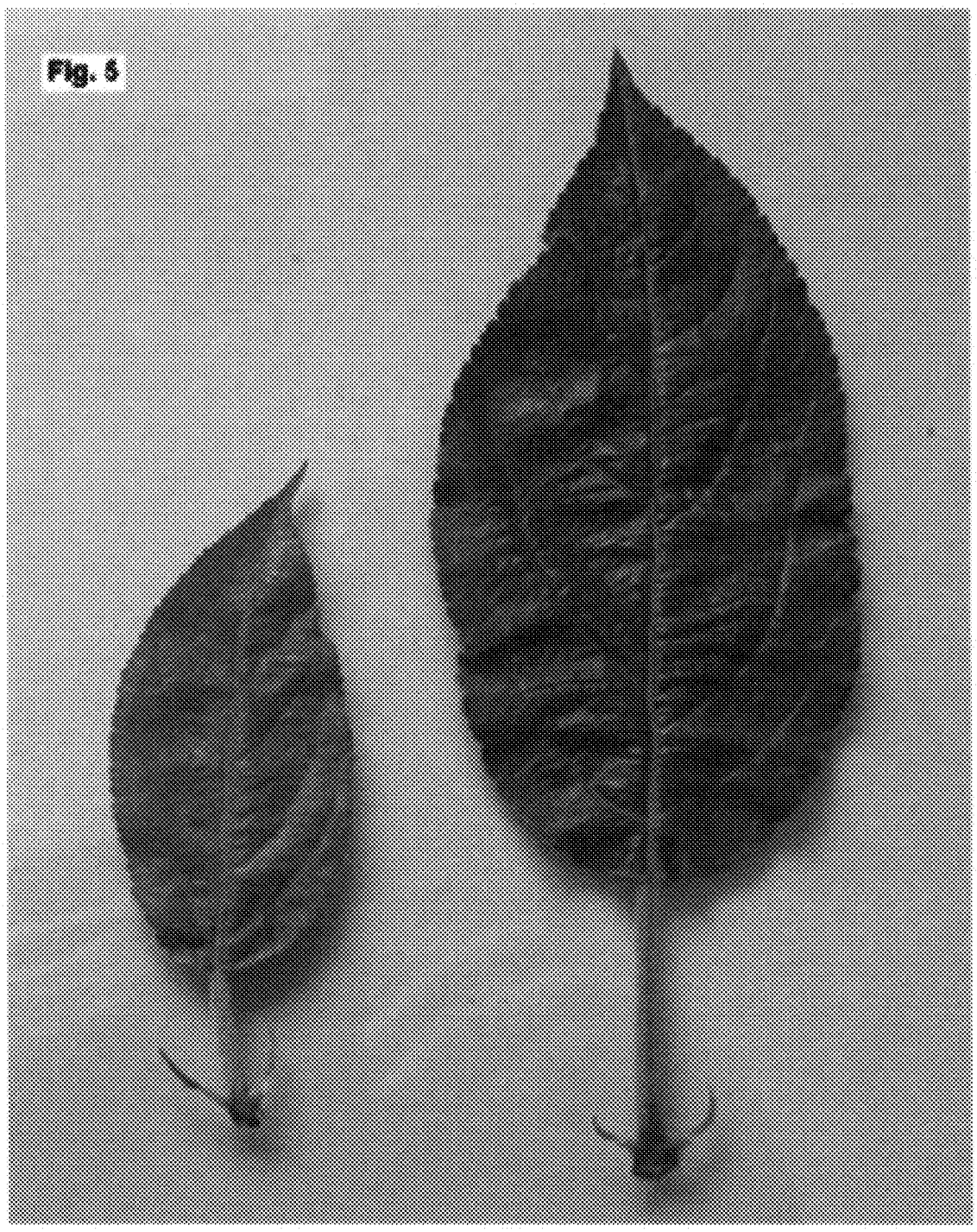
FIG. 5 shows a close-up view of the young and mature leaves of the new variety.
Figure 6:
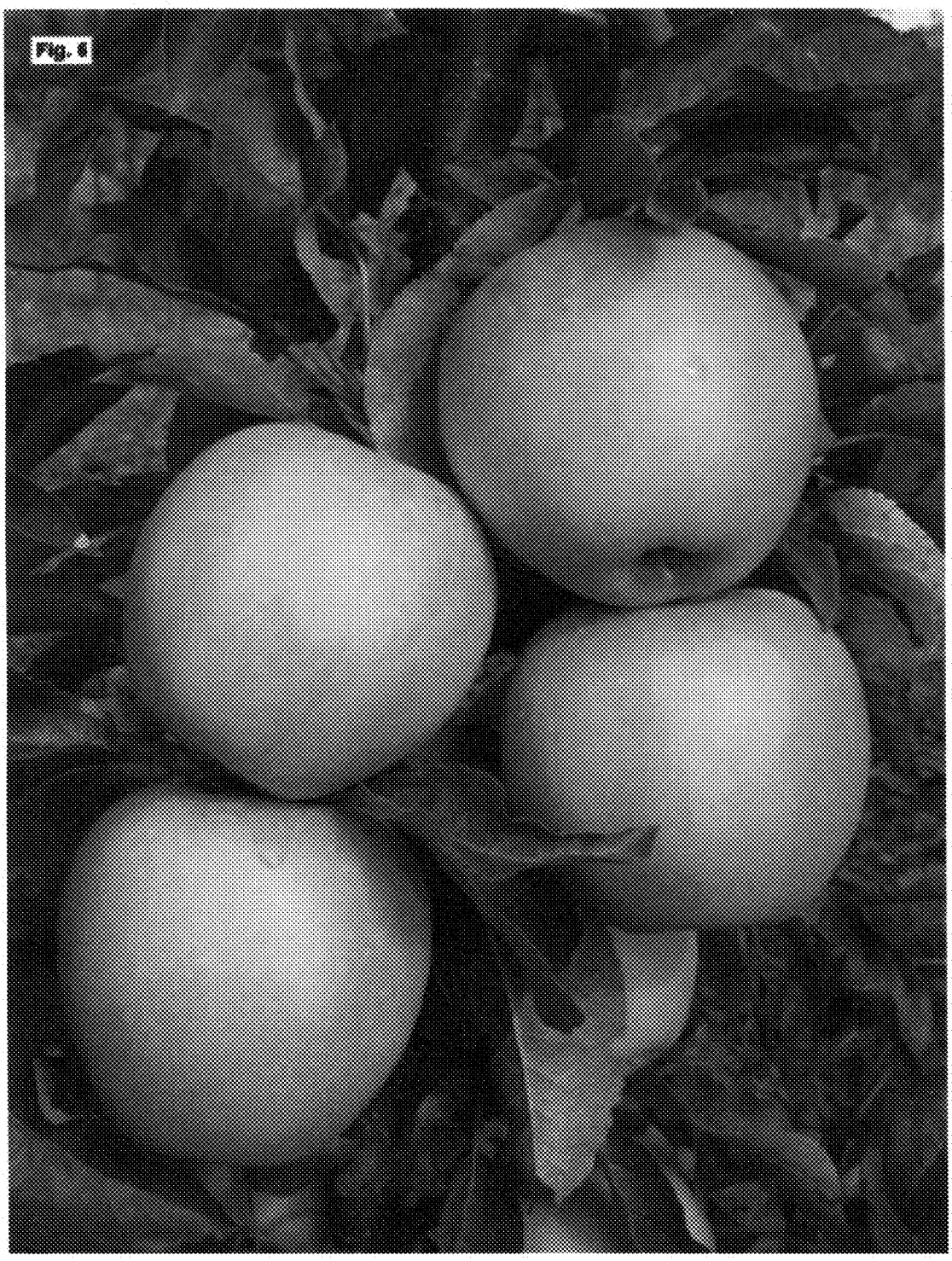
FIG. 6 shows a close-up view of the fruits of the new variety at picking maturity.

The following detailed description sets forth the characteristics of the new cultivar. The new variety was grown under natural field conditions in The Czech Republic. The growing area is 310 m above sea level with a mean annual temperature of 7.7° C. and a mean annual precipitation of 680 mm. The following fertilizer combination was used (Kg/ha/year): 55 parts nitrogen, 25 parts phosphorous, 60 parts potassium, 55 parts calcium, and 5 parts magnesium. Color references are primarily to The R.H.S. Colour Chart of The Royal Horticultural Society of London and were identified under natural light.

TREE

Age: 10 years from sowing.
Size: 3.4 m high, 0.5 m wide.
Vigor: Weak.
Density: Thick.
Form: Erect and compact; free of conventional side branches.
Production: Very precocious.
Growth Type: Columnar.
Bearing: Mainly on spurs.
Trunk:
- *Size.*—Approximately 7 cm in diameter at 30 cm from the soil line.
- *Surface texture.*—Smooth to slightly rough.
- *Bark color.*—174A.
- *Lenticels* (100 *cm above ground*).—Length: 2 mm to 4 mm. Width: 1 mm to 1.5 mm. Color: 156B. Density: Approximately 3 lenticels per 1 $cm^2$.

Branches:
- *Overall description.*—A conventional branching system along the tree trunk is lacking.
- *Diameter.*—Very small.
- *Surface texture.*—Smooth.
- *Color.*—A one year old shoot is 183A; a two year old branch is from 183A to 187A.
- *Form.*—Straight.
- *Average crotch angle.*—About 45 degrees.
- *Bud arrangement.*—Alternate. Internode length: 1 to 1.5 cm.
- *Lenticels* (*on* 1-*year shoot*).—Length: Typically 1.2 mm to 1.5 mm. Width: Typically 0.8 mm to 1.0 mm. Shape: Oval. Density: Dense, with about 12 lenticels per 1 $cm^2$. Color: 156C.

Leaves (measured at the middle of growing shoot):
- *Length.*—About 100 mm to about 130 mm, averaging 118 mm.
- *Width.*—About 50 mm to about 70 mm, averaging about 63 mm.
- *Form.*—Oblong.
- *Texture.*—Smooth with a wavy surface.
- *Thickness.*—Moderately thick.
- *Base.*—Predominantly symmetric.
- *Apex.*—Acute; straight or moderately bent.
- *Margin.*—Bicrenate.
- *Pubescence.*—Upper surface: None present. Lower surface: Fine on veins.
- *Color.*—Young leaves: Upper surface: 144A. Lower surface: 144B. Mature leaves: Upper surface: 146A. Lower surface: 146C.
- *Stipules.*—Average number: 2. Arrangement: Opposite. Length: About 12 mm. Width: About 1.5 mm. Color: 146B.
- *Petiole.*—Shape: Straight with thickening and flattening at the base. Length: About 35 mm to about 45 mm, averaging about 40 mm. Diameter: About 3.0 mm in the middle. Color: 144C and partly 59C at the base.
- *Veins.*—Venation type: Net-like, medium dense. Color: Upper surface: 144D. Lower surface: 145C.

Flower buds:
- *Pedicel.*—Length: Typically in the range of 21-24 mm, with an average of 22 mm. Diameter: 1.8 mm on average. Color: 144B.
- *Bud.*—Length: 15 mm on average. Width: 10 mm on average. Color: 64A to 64B.

Flowers:
- *Bloom timing.*—Medium to late; similar to 'Golden Delicious'.
- *Blooming period.*—Medium to long; about 8 days and depends on weather conditions.
- *Pollination requirements.*—Self-sterile, needs pollinators such as the common scab-resistant pollinator *Malus*×*Zumi* 'Golden Hornet'.
- *Number of flowers per cluster.*—5 to 6.
- *Fragrance.*—Faint.
- *Petals.*—Number: 5. Length: From 28-32 mm, with an average of 30 mm. Width: From 18-22 mm, with an average of 20 mm. Shape: Oval. Aspect: Positioned overlapping. Margin: Entire. Texture and appearance: Soft and smooth. Color: When opening: Upper surface: 69B to 69D. Lower surface: 75A to 75D. Fully opened: Upper surface: 69C to 69D and partly 155C. Lower surface: 75A to 75D.
- *Sepals.*—Shape: Elongated and conical; pointed. Margin: Entire. Texture: Upper surface: Fine, colorless pubescence. Lower surface: Pubescence present. Length: 10 mm to 12 mm from the union. Width: 3 mm in the middle. Color: Upper surface: 144B to 145B with an apex of 59A. Lower surface: 144B with an apex of 59A.
- *Stamens.*—Number (per flower): 20. Filament length: 7-13 mm.
- *Anthers.*—Shape: Oval. Length: 2 mm. Color: 10B.
- *Pollen.*—Color: 11A. Amount (generally): Medium.
- *Pistils.*—Number: 1 pistil with 5 styles fused at the base. Length: 23 mm on average.
- *Style.*—Length: 18 mm on average. Color: 144C.
- *Stigma.*—Shape: Rounded. Color: 151A.

Fruit:
- *Maturity when described.*—Eating maturity—after 2 months in common storage.
- *Date of picking.*—Oct. 18, 2006.
- *Size.*—Axial diameter: Average of 70 mm. Transverse diameter: Average of 78 mm.
- *Form.*—Globose-conical to conical.
- *Cavity.*—Shape: Accuminate. Depth: Typically between 12 mm and 16 mm; average of 14 mm. Breadth: Typically between 30 mm and 32 mm; average of 31 mm.
- *Basin.*—Shape: Bowl-shaped. Depth: Between 5 mm and 7 mm. Width: Between 21 mm and 25 mm.

*Calyx.*—Persistent with semi-erect lobes, open; moderate crowning at the calyx end of the fruit.

Skin:

*Thickness.*—Medium to thin.

*Texture.*—Smooth, free of russet.

*Tendency to crack.*—Absent.

*Color.*—A slightly variable 54D to 29C color can occur on exposed fruit.

*Ground color.*—151A to 7A.

*Bloom or greasiness.*—None present.

Flesh:

*Aroma.*—Medium.

*Color.*—12C to 12D.

*Texture.*—Fine, juicy, firm and crisp.

*Eating quality.*—Very good with a pleasant flavor and well-balanced sugar to acid ratio.

Core:

*Bundle area.*—On longitudinal section—heart-shaped, height 18 mm, length 20 mm, core locules partly open.

*Bundle.*—Core lines linking the vascular strands are almost absent.

*Calyx tube.*—Cylindrical and short.

*Depth of tube to shoulder.*—12 mm; calyx tube itself is about 2 mm long.

*Styles.*—Persistent as dry residues.

*Stamens.*—Persistent as dry residues.

*Seed cells.*—Wall: Slightly cracked, not tufted. Depth: 8mm to 9 mm. Breadth: 3 mm to 4 mm. Longitudinal section: About 18 mm (length of seed cell).

Seeds:

*Number perfect.*—8.

*Number in one cell.*—1 to 2.

*Length.*—8 mm to 9 mm.

*Breadth.*—About 4 mm.

*Form.*—Long and conical with an acute tip.

*Color.*—175A to 175B.

Stem:

*Length.*—Typically between 25 and 35 mm; average of 30 mm.

*Width.*—1.9 mm on average.

*Color.*—152C.

Fruit Characteristics:

*Percent soluble solids.*—12.4 Brix.

*Titratable acidity.*—5.62 g/l.

*Penetrometer reading.*—6.1 kg/cm$^2$.

Use: Late dessert variety with a columnar tree type having very good eating quality that is primarily suitable for home gardens.

Shipping quality: Good.

Keeping quality: Good, approximately 4 months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab; mildew tolerance observed.

Pest resistance/susceptibility: None observed.

I claim:

1. A new and distinct variety of *Malus domestica* (Borkh.) apple tree substantially as is herein described and illustrated.

* * * * *